US005599665A

United States Patent [19]

Barbieri et al.

[11] Patent Number: 5,599,665

[45] Date of Patent: Feb. 4, 1997

[54] *PSEUDOMONAS AERUGINOSA* NUCLEIC ACIDS ENCODING EXOENZYME S ACTIVITY AND USE THEREOF IN DETECTING *PSEUDOMONAS AERUGINOSA* INFECTION

[75] Inventors: Joseph T. Barbieri, New Berlin; Dara W. Frank; Scott M. Kulich, both of West Allis, all of Wis.

[73] Assignee: MCW Research Foundation, Milwaukee, Wis.

[21] Appl. No.: 171,299

[22] Filed: Dec. 21, 1993

[51] Int. Cl.$^{6}$ .............................. C12Q 1/68; C12N 15/85

[52] U.S. Cl. .......................... 435/6; 435/320.1; 536/23.2; 536/23.7; 536/24.32

[58] Field of Search .................. 435/6, 320.1; 536/23.2, 536/23.7, 24.32; 935/78

[56] References Cited

U.S. PATENT DOCUMENTS 5,223,604 6/1993 Hodges et al. .......................... 530/327

OTHER PUBLICATIONS

Iglewski, et al., "*P. aeruginosa* exoenyme S: . . . distinct from Toxin A", 75 *Proc. Natl. Acad. Sci. USA* 3211–3215 (1978).

Thompson, et al., "Exoenzyme S: . . . Produced by *P. aeruginosa*" in Smulson and Sugimura (eds.), *Novel ADP–Ribosylations of Regulatory Enzymes and Proteins,* pp. 425–433 (1980).

Nicas, et al., "Isolation . . . in Production of Exoenzyme S", 45 *Infect. Immun.* 470–474 (1984).

Nicas, et al., "Contribution . . . Virulence of *P. aeruginosa*", 36 *Antibiot. Chemother.* 40–48 (1985).

Nicas, et al., "The Role of . . . with *P. aeruginosa*", 152 *J. Infect. Dis.* 716–721 (1985).

Nicas, et al., "Role of . . . Lung Infections", 4 *Eur. J. Clin. Microbiol.* 175–179 (1985).

Coburn, et al., "Several GTP Binding . . . Exoenzyme S", 264 *J. Biol. Chem.* 9004–9008 (1989).

Coburn, et al., "Exoenzyme S . . . Protein Vimentin", 57 *Infect. Immun.* 996–998 (1989).

Coburn, "*P. aeruginosa* Exoenzyme S", 175 *Curr. Topics Microbiol. Immunol.* 133–143 (1992).

Sokol, et al., "Cloning . . . exoenzyme S toxin gene", 8 *Microbiol. Pathogenesis* 243–257 (1990).

Coburn, et al., "*P. aeruginosa* Exoenzyme S . . . Activity", 266 *J. Biol. Chem.* 6438–6446 (1991).

Fu, et al., "The eukaryotic host factor . . . family", 90 *Proc. Natl. Acad. Sci. USA* 2320–2324 (1993).

Frank, et al., "Cloning . . . *trans*–Regulatory Locus . . . *P. aeruginosa*", 173 *J. Bacteriol.* 6460–6468 (1991).

Woods, et al., "Purification . . . Exoenzyme S", 55 *INfect. Immun.* 579–586 (1987).

Kulich, et al., "Purification . . . *P. aeruginosa* 388", 61 *Infect. Immun.* 307–313 (1993).

Kulich et al., *J. Biol. Chem.* 269(14), 10431–10437 (1994).

Lee et al., *Science* 239, 1288–1291 (1988).

Matthews et al, *Anal.Biochem.* 169, 1–25 (1988).

*Primary Examiner*—Kenneth R. Horlick
*Attorney, Agent, or Firm*—Quarles & Brady

[57] ABSTRACT

A genetic construct containing a coding region for exoenzyme S activity from *Pseudomonas aeruginosa* is disclosed. A essentially pure protein preparation of the 49 kDa form of exoenzyme S is also disclosed. The protein product of the genetic construct may be used to modify the RAS protein function in mammalian carcinomas, used as a vaccine, or used to diagnose *Pseudomonas aeruginosa* infection.

2 Claims, 9 Drawing Sheets

FIG. 6b

```
1     CTGCAGGCTGAGTACGCTCTCCTCGTCATTGGGCGTCGGGAGATCGAGAGCGAGAAAAAG   60

61    CTGGTGGATGGCGGCGCGGTAGAGTGGATTCATGGCGTGTTCCGAGTCACTGGAGGCGGC   120

121   CATTAGAGCAGTGCCAGCCCGGAGAGACTGTTAATCGTGGTTCTCTTTTTTTAGGTTTTG   180

181   CCGCTGCCGATTCCAGTGAAAAAACGGCGGCCAATCCTGATAGGCGATGGGGTTTCCCGT   240

241   TCCTAGACTGGCGGAGAAACATCAGGAGAAGGCAACCATCATGCATATTCAATCGCTTCA   300
                                              M  H  I  Q  S  L  Q
301   GCAGAGTCCGTCTTTCGCCGTCGAATTGCACCAGGCCGCCAGTGGGCGTTTGGGACAGAT   360
        Q  S  P  S  F  A  V  E  L  H  Q  A  A  S  G  R  L  G  Q  I
361   TGAGGCCCGCCAGGTCGCCACCCCCAGTGAAGCGCAGCAGTTGGCCCAGCGCCAGGACGC   420
        E  A  R  Q  V  A  T  P  S  E  A  Q  Q  L  A  Q  R  Q  D  A
421   GCCGAAGGGTGAGGGGCTGCTCGCTCGCCTGGGCGCGGCGCTCGTGCGTCCGTTCGTGGC   480
        P  K  G  E  G  L  L  A  R  L  G  A  A  L  V  R  P  F  V  A
481   GATCATGGACTGGCTGGGCAAACTGTTGGGCTCCCACGCCCGCACCGGCCCGCAGCCCAG   540
        I  M  D  W  L  G  K  L  L  G  S  H  A  R  T  G  P  Q  P  S
541   TCAGGACGCGCAGCCTGCGGTCATGTCCTCGGCCGTCGTGTTCAAGCAGATGGTGCTGCA   600
        Q  D  A  Q  P  A  V  M  S  S  A  V  V  F  K  Q  M  V  L  Q
601   GCAGGCATTGCCCATGACCTTGAAGGGACTCGACAAGGCGAGCGAGCTGGCGACCCTGAC   660
        Q  A  L  P  M  T  L  K  G  L  D  K  A  S  E  L  A  T  L  T
661   ACCGGAAGGACTGGCCCGGGAGCACTCCCGCCTGGCCAGCGGAGATGGGGCGCTGCGTTC   720
        P  E  G  L  A  R  E  H  S  R  L  A  S  G  D  G  A  L  R  S
721   GCTGAGCACCGCCTTGGCCGGCATTCGTGCCGGCAGCCAGGTCGAGGAGTCCCGTATCCA   780
        L  S  T  A  L  A  G  I  R  A  G  S  Q  V  E  E  S  R  I  Q
781   GGCTGGCCGCCTGCTCGAACGGAGCATCGGCGGGATCGCGCTGCAGCAGTGGGGCACCAC   840
        A  G  R  L  L  E  R  S  I  G  G  I  A  L  Q  Q  W  G  T  T
841   CGGCGGTGCCGCGAGTCAACTGGTGCTCGACGCAAGCCCGGAACTGCGGCGCGAAATCAC   900
        G  G  A  A  S  Q  L  V  L  D  A  S  P  E  L  R  R  E  I  T
901   CGACCAGTTGCATCAGGTAATGAGCGAGGTCGCACTGTTGCGCCAAGCGGTAGAGAGCGA   960
        D  Q  L  H  Q  V  M  S  E  V  A  L  L  R  Q  A  V  E  S  E
961   GGTCAGCAGAGTATCGGCCGACAAGGCGCTGGCGGATGGCCTGGTGAAGCGGTTCGGGGC   1020
        V  S  R  V  S  A  D  K  A  L  A  D  G  L  V  K  R  F  G  A
1021  GGATGCGGAAAAGTACCTGGGCAGACAGCCTGGTGGCATCCACAGTGACGCCGAAGTGAT   1080
        D  A  E  K  Y  L  G  R  Q  P  G  G  I  H  S  D  A  E  V  M
1081  GGCGCTTGGTCTCTACACCGGCATTCACTACGCGGACCTGAATCGCGCTCTGCGTCAGGG   1140
        A  L  G  L  Y  T  G  I  H  Y  A  D  L  N  R  A  L  R  Q  G
1141  GCAGGAGCTGGATGCGGGACAAAAGCTGATCGACCAAGGTATGTCCGCGGCCTTCGAGAA   1200
        Q  E  L  D  A  G  Q  K  L  I  D  Q  G  M  S  A  A  F  E  K
1201  GAGCGGACAGGCTGAACAGGTAGTGAAGACTTTCCGTGGCACCCGTGGCGGGGATGCCTT   1260
        S  G  Q  A  E  Q  V  V  K  T  F  R  G  T  R  G  G  D  A  F
1261  CAACGCAGTGGAAGAGGGCAAGGTTGGCCACGACGACGGCTATCTCTCCACCTCCCTGAA   1320
        N  A  V  E  E  G  K  V  G  H  D  D  G  Y  L  S  T  S  L  N
```

FIG. 6c

```
1321  CCCCGGTGTCGCGAGGAGCTTCGGGCAGGGCACGATATCCACCGTGTTCGGCAGGTCCGG  1380
       P  G  V  A  R  S  F  G  Q  G  T  I  S  T  V  F  G  R  S  G
1381  AATCGATGTCAGCGGGATATCGAACTACAAGAATGAAAAAGAGATTCTCTATAACAAAGA  1440
       I  D  V  S  G  I  S  N  Y  K  N  E  K  E  I  L  Y  N  K  E
1441  AACCGACATGCGCGTGCTGCTGAGCGCCAGCGATGAGCAGGGAGTGACCCGCCGGGTTCT  1500
       T  D  M  R  V  L  L  S  A  S  D  E  Q  G  V  T  R  R  V  L
1501  CGAAGAGGCGGCCCTGGGGGAGCAGAGTGGCCATAGCCAGGGACTGCTCGATGCTCTCGA  1560
       E  E  A  A  L  G  E  Q  S  G  H  S  Q  G  L  L  D  A  L  D
1561  CCTGGCAAGCAAACCGGAACGTTCAGGCGAGGTCCAGGAACAGGATGTACGCCTGAGGAT  1620
       L  A  S  K  P  E  R  S  G  E  V  Q  E  Q  D  V  R  L  R  M
1621  GCGCGGCCTTGATCTGGCCTGACCGGTCGTAAAAGAAAGACGTCACGAACGGACACCTTG  1680
       R  G  L  D  L  A  *
1681  GGGTGTCCGATTCTTGGCTCGGCAGCGGATCC  1712
```

*PSEUDOMONAS AERUGINOSA* NUCLEIC ACIDS ENCODING EXOENZYME S ACTIVITY AND USE THEREOF IN DETECTING *PSEUDOMONAS AERUGINOSA* INFECTION

FIELD OF THE INVENTION

The present invention relates generally to the isolation and uses of a genetic construct encoding a structural gene for exoenzyme S activity from *Pseudomonas aeruginosa.*

BACKGROUND OF THE INVENTION

*Pseudomonas aeruginosa* is an opportunistic pathogen affecting humans and is responsible for up to 20% of nosocomial infections and 3–6% of community-acquired infections. See Bodey, et al., *Rev. Infect. Dis.* 5(2):279–313 (1983). Individuals afflicted by certain medical conditions such as cystic fibrosis, leukemia, neutropenia, and burn wounds appear to be predisposed to *Pseudomonas aeruginosa* infections. See Bodey, et al., *Rev. Infect. Dis.* 5(2):279–313 (1983); Wood, *Hosp. Pract.* 11:91–100 (1976).

*Pseudomonas aeruginosa* produces both cell-associated and secreted factors which contribute to its pathogenesis. Nicas, et al., *Can. J. Microbiol.* 31:387–392 (1985). One class of virulence factors produced by *Pseudomonas aeruginosa* is the ADP-ribosyltransferases. *Pseudomonas aeruginosa* produces two ADP-ribosyltransferases, exotoxin A and exoenzyme S, which can be differentiated biochemically by target protein specificity, Coburn, et. al., *Infect. Immun.* 57(3):996–8 (1989), Coburn, et al., *Infect. Immun.* 59(11):4259–62 (1991), Iglewski, et al., *Proc. Natl. Acad. Sci. U.S.A.* 72(6):2284–8 (1975), Iglewski, et al., *Proc. Natl. Acad. Sci. U.S.A.* 75(7):3211–5 (1978); by the amino acid residue of the target protein that is ADP-ribosylated, Coburn, et al., *J. Biol. Chem.* 264(15):9004–8 (1989); Iglewski,et al., ADP-ribosylation of elongation factor 2 in animal cells. p. 511–524 (1990) In Moss and Vaughan (ed.), ADP-Ribosylating Toxins and G Proteins: Insights into Signal Transduction. American Society for Microbiology, Washington D.C.; and by their requirements for activation of enzymatic activity in vitro, Iglewski, et al., *Proc. Natl. Acad. Sci. U.S.A.* 75(7):3211–5 (1978) and Coburn, et al., *J. Biol. Chem.* 266(10):6438–46 (1991).

Exoenzyme S has been implicated as a mediator of *Pseudomonas aeruginosa* pathogenesis in burn wounds and chronic lung infections. Tn-1 mutagenesis of *Pseudomonas aeruginosa* strain 388 produced a mutant strain termed 388 exs1::Tn1 which lacked detectable exoenzyme S activity in culture supernatant fluids. See Nicas, et al., *Infect. Immun.* 45(2):470–4 (1984). In the burned mouse model, strain 388 exs1::Tn1 was greater than 2,000-fold less toxic than the wild type strain 388. Strain 388 exs1::Tn1 was not defective in its ability to colonize burn wounds, but showed decreased ability to disseminate from burn wounds when compared to the wild type strain 388. Antibody prepared against exoenzyme S protected burned mice against challenge with wild type strain 388. Nicas, et al., *Antibiot. Chemother.* 36(40):40–8 (1985).

In a chronic rat lung infection model, strain 388 exs1::Tn1 colonized host tissue as effectively as wild type strain 388, but histological examination showed that strain 388 exs1::Tn1 did not elicit as severe lung tissue pathology as that caused by wild type strain 388. See Nicas, et al., *Eur. J. Clin. Microbiol.* 4(2):175–9 (1985). Woods and colleagues, Woods, et al., *Euro. J. Clin. Microbiol.* 4(2):163–9 (1985), observed similar results in the rat lung model, utilizing transposon mutants of *Pseudomonas aeruginosa* strain DG1 that possessed a negative exoenzyme S phenotype. Together, these data have implicated exoenzyme S as a mediator of *Pseudomonas aeruginosa* dissemination from localized infections and have targeted exoenzyme S as a potential protective immunogen for vaccine development against *Pseudomonas aeruginosa* infections.

Exoenzyme S appears to be secreted into the culture medium as both a 53 kDa form and a 49 kDa form. See Nicas, et al., *Infect. Immun.* 45(2):470–4 (1984). The 49 kDa form of exoenzyme S possesses enzymatic activity following elution from sodium dodecyl sulfate (SDS)-polyacrylamide gels (PAGs), Coburn, et al., *J. Biol. Chem.* 266(10):6438–46 (1991) and Nicas, et al., *Infect. Immun.* 45(2):470–4 (1984), and has been designated the enzymatically active form of exoenzyme S. The 53 kDa form of exoenzyme S, which does not possess any apparent ADP-ribosyltransferase activity in vitro, Nicas, et al., *Infect. Immun.* 45(2):470–4 (1984), appears to be related to the 49 kDa form of exoenzyme S based upon apparent immunological cross-reactivity, Nicas, et al., *Infect. Immun.* 45(2):470–4 (1984) and Kulich, et al., *Infect. Immun.* 61(1):307–13 (1993); possession of a common amino-terminal amino acid sequence, Coburn, In Aktories (ed.), *Current topics in microbiology and immunology:ADP-ribosylating toxins.* 175:133–143 (1992) Springer-Verlag, Berlin; and sharing of common peptides following proteolytic and cyanogen bromide cleavage, Iglewski, 249–265 In Hardegree M. C. and Tu, A. T. (eds), *Handbook of toxins*, vol. 4, Marcel-Dekker, New York (1988). The absolute biochemical and genetic relationship between the 53 kDa form and the 49 kDa form of exoenzyme S has not been resolved. These data are consistent with the 53 kDa form and the 49 kDa form of exoenzyme S existing in a precursor-proteolytic product relationship and that the 53 kDa form of exoenzyme S undergoes a carboxyl-terminal cleavage to yield the enzymatically active 49 kDa form of exoenzyme S. The observation that other bacterial ADP-ribosyltransferases undergo proteolytic activation lends some precedence to this hypothesis. See Drazin, et al., *J. Biol. Chem.* 246(5):1504–10 (1971); Mekalanos, et al., *J. Biol. Chem.* 254(13):5855–61 (1979); and Vasil, et al., *Infect. I Immun.* 16(1):353–61 (1977).

The present invention focuses on the biochemical and molecular characterization of exoenzyme S as an ADP-ribosyltransferase. As prior exoenzyme S studies have relied on denatured, mixed preparations of the 49 and 53 kDa form, we are the first to show conclusively that exoenzyme S activity copurifies with two proteins possessing apparent molecular masses of 53 and 49 kDa respectively and that α-49 kDa protein IgG inhibits exoenzyme S mediated ADP-ribosyltransferase activity in a dose-dependent fashion Kulich, et al., *Infect. Immun.* 61(1):307–13 (1993). (This article is incorporated by reference as if fully set forth herein.) In the present invention, we also disclose the purification and proteolytic characterization of the 49 kDa form of exoenzyme S and the cloning of the structural gene for the 49 kDa form of exoenzyme S (exoS).

SUMMARY OF THE INVENTION

One aspect of the invention provides a genetic construct containing a coding region for the exoenzyme S activity from *Pseudomonas aeruginosa.* In a preferred embodiment, the genetic construct also contains appropriate regulatory sequences so that the coding region can be expressed in a mammalian, yeast, plant or bacterial host. The coding region may be any size as long as it contains a coding sequence that when expressed exhibits exoenzyme S activity. The activity may be determined by using a method which quantifies the ADP-ribosyltransferase activity using soy bean trysin inhibitor as the target for ADP-ribosylation. See description below and Kulich, et al., 61 *Infect. Immun.* 307–313 (1993).

Another aspect of the present invention provides a genetic construct containing a coding region for the 49 kDa form of exoenzyme S from *Pseudomonas aeruginosa* . Preferably the sequence of the coding region for this genetic construct is according to SEQ ID NO: 1.

Another aspect of the present invention is an essentially pure preparation of the 49 kDa form of exoenzyme S. By "essentially pure" we mean that the preparation of the present invention contains less than 10% contamination with the 53 kDa form of exoenzyme S and no other constituents that would substantially interfere with exoenzyme S activity, such as SDS. Most preferably, an essentially pure protein preparation contains no detectible 53 kDa form of exoenzyme S.

Another aspect of the present invention permits a vaccine to prevent infection by *Pseudomonas aeruginosa* . For example, vaccine candidates may possess genetically engineered nontoxic forms of exoenzyme S in *Pseudomonas aeruginosa*. This type of vaccine may be of importance in a hospital setting as *Pseudomonas aeruginosa* is a major source of hospital acquired infections. Also, cystic fibrosis and burn patients are susceptible to Pseudomonas infections.

Still another aspect of the present invention provides a method of modifying the RAS protein function in mammalian carcinomas wherein the mammal is treated with the protein product of the genetic construct containing a coding region for exoenzyme S activity from *Pseudomonas aeruginosa.*

Another potential application of the present invention is the use of the genetic construct encoding the active exoenzyme S protein as a diagnostic tool. Exoenzyme S production correlates to the development of disseminated Pseudomonas infections and sepsis. The development of techniques to detect strains that express exoenzyme S in compromised patients may lead to earlier and more effective therapeutic intervention.

One particular advantage of the genetic constructs of the present invention is that they are useful for the study of exoenzyme S regulation and production from *Pseudomonas aeruginosa* and for the study of the regulation of cancerous cell growth.

Another advantage of the genetic constructs of the present invention is that they may be used to create a preparation of the 49 kDa form of exoenzyme S that need not be isolated from Pseudomonas bacteria. Additionally, a large amount of this protein will become available for further studies and analysis.

An object of the present invention therefore is providing genetic constructs and protein preparations of the above kind. Additionally, another object of the present invention is to use the genetic constructs and protein preparations described above to vaccinate an animal against Pseudomonas infection. A method of modifying the Ras protein function in mammalian carcinomas is also an object of the present invention. Additionally, an object of the present invention is to create a diagnostic tool for Pseudomonas infections. These and still other objects and advantages of the present invention will be apparent from the description below.

BRIEF DESCRIPTION OF THE DRAWINGS

FIG. 6A represents a restriction endonuclease map and FIG. 6B is a nucleotide sequence of exoS (also at SEQ ID NO: 1) and amino acid sequence of the 49 kDa form of exoenzyme S through nucleotide 1320; and FIG. 6C is the continued nucleotide sequence of exoS (also at SEQ ID NO:1) and continued amino acid sequence of the 49 form of exoenzyme S.

DESCRIPTION OF THE PREFERRED EMBODIMENTS

Figure 1:
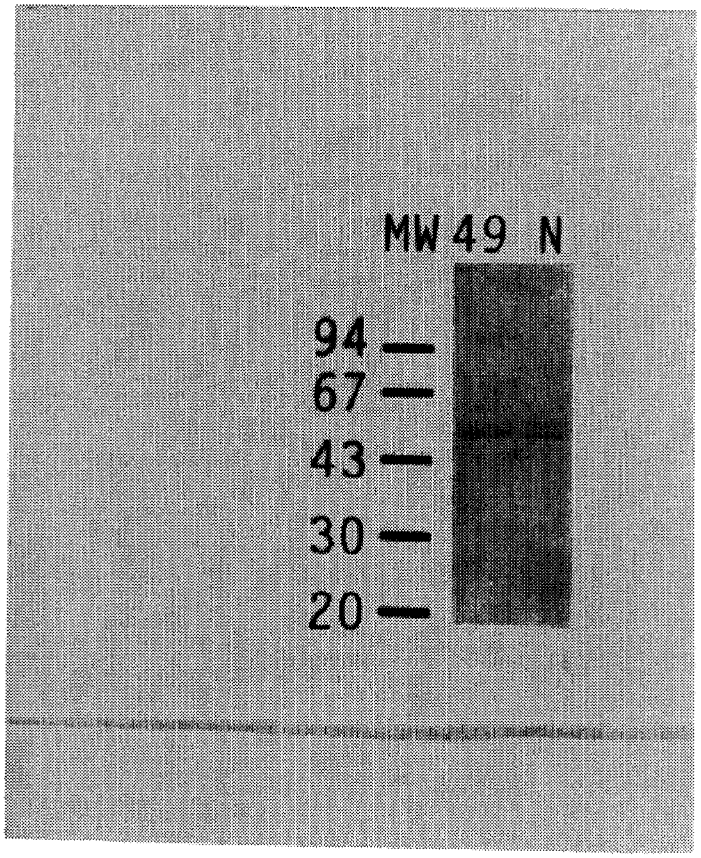
FIG. 1 depicts SDS-PAGE analysis of the native exoenzyme S and purified 49 kDa form of the exoenzyme S.

One embodiment of the present invention is a genetic construct encoding *Pseudomonas aeruginosa* exoenzyme S activity. Preferably, this genetic construct contains a coding sequence according to SEQ ID NO: 1 and appropriate regulatory sequences such that the coding region of SEQ ID NO: 1 may be expressed in a mammalian or bacterial host. However, the coding region need not be identical to SEQ ID NO: 1. Minor deletions, additions, point mutations and sequence variables may also result in a sequence that encodes exoenzyme S activity. One would evaluate a candidate sequence as described below by its ability to encode a functioning exoenzyme S activity.

The following "Materials and Methods" section discloses the inventors purification of native exoenzyme S, determination of exoenzyme S activity, characterization of the purified 49 kDa form of exoenzyme S, construction of nucleic acid probes specific for the 49 kDa form of exoenzyme S and selection of a genetic construct containing the exoenzyme S activity. Having characterized the exoenzyme S gene and protein, we have enabled one skilled in the art of molecular biology to obtain a genetic construct capable of expressing exoenzyme S in a manner different from the one we employed. For example, SEQ ID NO: 1 (the sequence of the exoS gene) enables one skilled in the art to create many different probes capable of retrieving the exoS sequence from an appropriate library prepared from *Pseudomonas aeruginosa* . Additionally, our characterization of the 49 kDa exoenzyme S protein (described below) enables one skilled in the art to determine whether a candidate nucleic acid construct expresses a protein product which physically corresponds to the native 49 kDa exoenzyme S protein.

MATERIALS AND METHODS

Purification of Native Exoenzyme S.

Native exoenzyme S was purified from the culture supernatant fluid of *Pseudomonas aeruginosa* strain 388 as previously described in Kulich, et al., *Infect. Immun.*

61(1):307–13 (1993). In brief, proteins in the spent culture medium were concentrated and subjected to DEAE Sephacel chromatography. Fractions containing exoenzyme S ADP-ribosyltransferase activity were pooled and concentrated by XM300 ultrafiltration.

Strain 388 can be obtained from the laboratories of B. H. Iglewski (University of Rochester, Rochester, N.Y.), D. W. Frank, and J. T. Barbieri (Medical College of Wisconsin, Milwaukee, Wis.). *Pseudomonas aeruginosa* 388 is not available in the American Type Culture Collection electronic listing. Strains which are appropriate for the purification of an enzymatically active for (49 kDa) of exoenzyme S include *Pseudomonas aeruginosa* PAK. Another appropriate strain is strain PAO1, available from ATCC.

Other published purification protocols lack specific activity measurements (Coburn, J., A. V. Kane, L. Feig, and D. M. Gill (1991). *Pseudomonas aeruginosa* exoenzyme S requires a eukaryotic protein for ADP-ribosyltransferase activity. *J. Biol. Chem.* 266:9004–9008 and Nicas, T. I., and B. H. Iglewski (1984). Isolation and characterization of transposon-induced mutants of *Pseudomonas aeruginosa* deficient in production of exoenzyme S. *Infect. Immun.* 45:470–474.) or enrich for toxic forms of exoenzyme S (Woods, D. E., and J. U. Oue. (1987). Purification of *Pseudomonas aeruginosa* exoenzyme S. *Infect. Immun.* 55:579–586).

Purification of the 49 kDa Form of Exoenzyme S.

The 49 kDa form of exoenzyme S was purified from native exoenzyme S by electroelution as described by Hunkapiller et al., with minor modifications. See Hunkapiller, et al., *Methods In Enzymology.* 91(227):227–36 (1983). (This article is incorporated by reference as if fully set forth herein). In brief, native exoenzyme S was subjected to 10% reduced SDS-polyacrylamide gel electrophoresis (SDS-PAGE), Laemmli, U. K. Nature (London). 227:680–5 (1970), in the presence of 0.1 mM sodium thioglycolate. Following electrophoresis, proteins were stained with Coomassie blue (5 min at 4° C.) followed by destaining (5 min at 4° C.). The region of the gel containing the 49 kDa form of exoenzyme S was excised and subjected to electroelution at 50 V overnight at room temperature in a microconcentrator cup (Isco) equipped with a 3–5 kDa molecular weight cut off membrane (Spectrapor). The electroeluted protein was subjected to ultrafiltration in a Centricon 30 microconcentrator (Amicon). The retentate was washed with $H_2O$ to removed excess SDS. By excess SDS we mean an amount of SDS that interferes with the exoenzyme S activity. The final Centricon 30 retentate was termed "purified 49 kDa form of exoenzyme S." This protein contains less than 1% 53 kDa form of exoenzyme S.

One of skill in the art will recognize upon examination of the above-identified protocol for isolating a preparation of 49 kDa form of exoenzyme S that other protein isolation methods might be equally suitable to obtain an essentially pure form of the 49 kDa form. Alternatively, the 49 kDa form may be obtained by recombinant techniques using the genetic construct described below. A preparation of the present invention preferably no 53 kDa form of exoenzyme S. Most preferably, the preparation contains less than 0% of the 53 kDa form. Applicants note that a preparation obtained from use of a genetic construct encoding the 49 kDa form of exoenzyme S will contain no 53 kDa form of the exoenzyme S.

Ion-Pair Extraction of Purified 49 kDa Form of Exoenzyme S.

SDS and Coomassie blue were removed from purified 49 kDa form of exoenzyme S by ion-pair extraction utilizing a solvent composed of acetone: glacial acetic acid: triethylamine (90:5:5/V:V:V) Henderson, et al., Anal. Biochem. 93(1):153–7 (1979). The protein precipitate following ion-pair extraction, which was termed ion-pair extracted 49 kDa form of exoenzyme S, was suspended in one of three buffers: a) 25 mM Tris-HCl (pH 7.6) containing varying concentrations of urea and Triton X-100 to assess enzymatic activity, b) SDS-PAGE sample buffer containing β-mercaptoethanol to assess purity and recovery following ion-pair extraction, or c) 40% acetonitrile in $H_2O$ (ACN) to assess protease sensitivity.

Determination of Exoenzyme S Activity.

Quantitation of the ADP-ribosyltransferase activity of native exoenzyme S and the purified and ion-pair extracted 49 kDa forms of exoenzyme S was determined using soybean trypsin inhibitor (SBTI) as the target for ADP-ribosylation. See. *Kulich*, et al., *Infect. Immun.* 61(1):307–13 (1993). Reaction mixtures contained in a final volume of 40 μl: 0.2 M sodium acetate (pH 6.0), 30 μM SBTI, 30 μM [adenylate phosphate$^{32}$P]-NAD (specific activity, 0.1 Ci/mmol), 0.1 μM purified recombinant FAS (Fu, et all, *Proc. Natl. Acad. Sci. U.S.A.* 90(6):2320–4 (1993)) and 0.3 pmol of 49 kDa form of exoenzyme S equivalent. Assays were performed at 37° C. We obtained a specific activity of at least 160 mol/min/mol 49 kDa.

If one wishes to evaluate a candidate nucleic acid clone, one would perform the assay described above with the product of the candidate clone. An enzyme activity of at least 80 mol/min/mol 49 kDa would indicate a clone with an appropriate amount of exoenzyme S activity. Most preferably, the expression product would have an enzymatic activity of at least 160 mol/min/mol 49 kDa.

Proteolytic Digestion of Purified 49 kDa Form of Exoenzyme S.

Purified 49 kDa form of exoenzyme S was subjected to proteolysis with the indicated proteases. Digestions were performed at 37° C. in 10μl reaction mixtures. Trypsin, chymotrypsin, and thermolysin digestions were performed in 100 mM Tris-HCl (pH 8.0), 5 mM $CaCl_2$, and the indicated amounts of urea, Triton X-100, CHAPS, or ACN. See Riviere, et al., *Techniques in Protein Chemistry II.* 170–179 (1991). V8 protease digestions were performed in 100 mM potassium phosphate (pH 7.8) containing 2 mM EDTA. The indicated amount of protease was added to start the reaction. An aliquot of each reaction mixture was subjected to SDS-PAGE containing γ-mercaptoethanol and the gels were stained with Coomassie blue. To assess the effect of NAD and FAS on the proteolysis of purified 49 kDa form of exoenzyme S, the reaction mixtures were incubated for 30 min with 1 mM NAD and/or 0.2 mg of wheat germ extract, Chung, et al., *Infect. Immun.* 16(3): 832–41 (1977), per ml as a source of FAS.

Reverse-Phase HPLC (RP-HPLC) and Amino Acid Sequence Analysis of Tryptic Peptides of Ion-Pair Extracted 49 kDa Form of Exoenzyme S.

Reaction mixture (300 μl) contained: 0.1 M Tris-HCl (pH 8.0), 5 mM $CaCl_2$, 30% ACN, 140 pmol of ion-pair extracted 49 kDa form of exoenzyme S, and trypsin 10% (w/w). The reaction mixture was incubated for 16 h at 37° C. when a second addition of 10% (w/w) trypsin was made followed by a 4 h incubation. The tryptic digest was diluted to 7.5% ACN, acidified to 1% trifluroacetic acid (TFA), and subjected to RP-HPLC (Beckman μbondapak column, 5 μm particles). Peptides were eluted in 0.1% TFA with a linear 5 to 75% ACN gradient at a 1.0 ml /min flow rate. Peptides were monitored by absorbance at 215 nm. Peptides were collected, dried, and subjected to amino acid sequence analysis as previously described. See Barbieri, et al., *J. Bacteriol.* 171(8):4362–9 (1989).

Amplification of Nucleic Acid Probes Specific for the 49 kDa Form of Exoenzyme S.

Two strategies were utilized to generate nucleic acid probes which were specific for the 49 kDa form of exoenzyme S; DNA amplification with oligonucleotides containing 5' restriction endonuclease cleavage sites and DNA amplification with nested oligonucleotides. Degeneracy of the oligonucleotides was minimized by using the observed preferred codon usage within structural genes of *Pseudomonas aeruginosa*. See West, et al., *Nucl. Acids Res.* 16(19):9323–35 (1988). Templates were amplified in 25 µl reaction mixtures containing 200 µM dNTPs, taq buffer, 2 mM MgCl$_2$, and taq DNA polymerase.

(a) DNA amplification with oligonucleotides containing 5' restriction endonuclease cleavage sites. A DNA fragment specific for the 19 amino-terminal amino acid residues of the 49 kDa form of exoenzyme S, Kulich, et al., *Infect. Immun.* 61(1):307–13 (1993), was amplified from *Pseudomonas aeruginosa* 388 chromosomal DNA that had been digested with DraI using 10 pmol of oligonucleotides which contained EcoRI and BamHI restriction sites at the 5' end of the sense oligonucleotide CATGGATCCGAATTCATGCAYATCCAR-ATCCARTCSYT (SEQ ID NO: 2) and HindIII and SalI restriction sites at the 5' end of the antisense oligonucleotide CATGGATTCGAATTCGARCTSCAYCARGCSGC (SEQ ID NO: 3). The amplification scheme was as follows: Precycle, 90 s incubation at 97° C.; cycles 1–5, 97° C. for 30s, 35° C. for 60 s, and 68° C. for 60 s; cycles 6–35, 94° C. for 30 s and 68° C. for 180 s; cycle 36, 68° C. for 300 s. The DNA in this reaction mixture was extracted with glass fog (MERMAID, Biol01), digested with EcoRI and HindIII, and ligated into M13mp18 and M13mp19 at the same restriction sites. Recombinant M13 phage where plaque purified and the amplified DNA inserts were subjected to dideoxy DNA sequence analysis. See Sanger, et al., *J. Mol. Biol.* 143(2):161–78 (1980). Three recombinant M13 phage were determined to possess DNA fragments encoding the 19 amino terminal amino acids of the 49 kDa form of exoenzyme S. This DNA fragment was termed the amino-terminal probe.

(b) DNA amplification with nested oligonucleotides. See Zolkiewska, et al., *Proc. Natl. Acad. Sci. U.S.A.* 89:11352–56 (1992). Sense and antisense oligonucleotides were synthesized from the determined amino acid sequence of the 55 min and 48 min tryptic peptides of the 49 kDa form of exoenzyme S. After two sequential amplifications (see amplification scheme below), a specific DNA fragment was observed using the sense 48 min oligonucleotide (48-POS) TTCGGYCARGGYACSAT (SEQ ID NO: 4) and two nested antisense 55 min oligonucleotides (55-1NEG) TGYTCRCCSAGSGCSGC (SEQ ID NO: 5) and (55-2NEG) CCSAGSGCSGCYTCYTC (SEQ ID NO: 6). Amplification scheme; amplification #1, *Pseudomonas aeruginosa* 388 chromosomal DNA that had been digested with DraI was amplified with 50 pmol of 48-POS and 55-1NEG as follows: precycle, 90 s incubation at 97° C.; 1–5 cycles, 97° C. for 30 s, 35° C. for 60 s, and 60° C. for 60 s; cycles 6–10, 94° C. for 30 s, 40° C. for 60 s, and 68° C. for 60 s; cycles 1115 , 94° C. for 30 s, 45° C. for 60 s, and 60° C. for 60 s; cycles 16–30, 94° C. for 30 s, 50° C. for 60 s, and 68° C. for 60 s; and cycle 31, 68° C. for 300 s; amplification #2, 1 µl of amplification mix #1 was subjected to a second amplification using 50 pmol of 48-POS and 55-2NEG as follows: precycle, 90 s incubation at 97° C.; cycles 1–5, 97° C. for 30s, 45° C. for 68 s, and 60° C. for 60 s; cycles 6–25, 94° C. for 30 s, 50° C. for 60 s, and 68° C. for 60 s; and cycle 26, 68° C. for 300 s. The DNA in this reaction mixture was extracted with glass fog (MERMAID, Biol01), treated with Klenow fragment, and ligated into HindIII digested M13mp18. Recombinant M13 phage containing amplified DNA were plaque purified and the amplified DNA was subjected to dideoxy DNA sequence analysis. One recombinant M13 phage was determined to possess a DNA fragment that contained an open reading frame which encoded the appropriate sequence of the 48 and 55 min tryptic peptides. This DNA fragment was termed the internal probe.

Southern Blot Hybridization and Screening of a Cosmid Library of Strain 388 DNA Using the Amplified 49 kDa Form of Exoenzyme S Probes.

Chromosomal DNA from *Pseudomonas aeruginosa* strain 388 was isolated by a modification of a protocol outlined by Meade et al. See Meade, et al., *J. Bacteriol.* 149:114–122 (1982). After lysis and extraction of nucleic acids from bacterial cells, 5 ml of lysate was added to 4.8 g of CsCl. The solution was subjected to ultracentrifugation at 250,000×g at 20° C. for 18 h in a VTi80 rotor (Beckman Instruments, Fullerton, Calif.). Viscous material corresponding to chromosomal DNA was removed and dialyzed overnight against 10 mM Tris-HCl (pH 8.0) containing 1 mM Na$_2$EDTA. After dialysis, chromosomal DNA was digested to completion with either BamHI, EcoRI, or HindIII restriction endonucleases (BRL, Gaithersburg, Md.). Fragments were separated on 0.9% agarose gels and transferred to nitrocellulose paper using a Pharmacia Vacugene apparatus. HindIII-cleaved lambda molecular weight markers were transferred and detected by hybridization for molecular weight estimations.

Colony blot hybridizations, Maniatis, et al., *Molecular cloning: a laboratory manual*. Cold Spring Harbor Laboratory, Cold Spring Harbor, N.Y. (1982), were performed to detect cosmid clones with sequences homologous to the internal probe. A cosmid bank containing 388 chromosomal DNA was constructed in pLAFR in *E. coli* HB101. This *Pseudomonas aeruginosa* strain 388 cosmid bank was engineered by T. Nicas, L. Hanne and B. H. Iglewski (University of Rochester). Plasmid DNA isolated from cosmid clones which bound the internal probe was subjected to Southern blot analysis using both the amino-terminal and internal probes.

DNA probes for both Southern blot analysis and colony blot hybridizations were isolated from PCR reactions following electrophoresis on 1% agarose gels buffered with Tris-acetate. See Maniatis, et al., *Molecular cloning: a laboratory manual*. Cold Spring Harbor Laboratory, Cold Spring Harbor, N.Y. (1982). Isolated fragments were purified using glass fog (MERMAID, Biol01) and labeled with [$\alpha$–$^{32}$P]dCTP (3,000 Ci/mmol; New England Nuclear Research Products) using a random primer DNA labeling system (BRL, Gaithersburg, Md.).

The nucleotide sequence of the sense and antisense strands of the 1712 bp PstI-BamHIII DNA fragment was determined by dideoxy DNA sequencing using two methods, the deaza Taq Track sequencing system (Promega Biochemicals) and the deaza Sequenase sequencing system (USB). This sequence is reported in SEQ ID NO: 1. The structural gene encoding the 49 kDa form of exoenzyme S (EXOS) was subjected to FASTA and BESTFIT analysis using GCG software, version 8.

RESULTS

Purification of the 49 kDa Form of Exoenzyme S.

Native exoenzyme S was purified from the culture supernatant fluid of *Pseudomonas aeruginosa* 388. FIG. 1 is an SDS-PAGE analysis of native exoenzyme S and purified 49 kDa form of exoenzyme S. Native exoenzyme S contains a heterogeneous population of proteins (FIG. 1, lane N) with two prominent proteins of apparent molecular masses of 53 and 49 kDa. This was consistent with previous descriptions of the exoenzyme S. See Nicas, et al., *Infect. Immun.* 45(2):470–4(1984) and Kulich, et al., *Infect. Immun.* 61(1):307–13(1993). Referring to FIG. 1, native exoenzyme S (N) and purified 49 kDa form of exoenzyme S (49) were subjected to reduced 10% SDS-PAGE. Gels were stained for protein with Coomassie blue. Lane MW indicates the relative migration of protein standards with molecular weights 94, 67, 43, 30, and 20 kDa. The 49 kDa form of exoenzyme S was purified from native exoenzyme S using an electroelution procedure with an average recovery of 70% (range=32%–93%, n=5). This procedure separated the 49 kDa form of exoenzyme S from contaminating proteins present in preparations of native exoenzyme S and yielded sufficient amounts of the 49 kDa protein for biochemical analysis. This material was termed "purified 49 kDa form of exoenzyme S."

ADP-Ribosyltransferase Activity of Purified 49 kDa Form of Exoenzyme S.

Although several laboratories have successfully recovered ADP-ribosyltransferase activity following elution of the 49 kDa form of exoenzyme S from SDS-PAGs (Coburn, et al., *J. Biol. Chem.* 266(10):6438–46 (1991) and Nicas, et al., *Infect. Immun.* 45(2):470–4 (1984)) purified 49 kDa form of exoenzyme S that was prepared by the electroelution protocol that we followed did not possess detectable ADP-ribosyltransferase activity. One explanation for the lack of enzymatic activity in our preparations was due to the presence of SDS in the protein preparations, since SDS inhibits exoenzyme S activity. Purified 49 kDa form of exoenzyme S was subjected to ion-pair extraction to remove both Coomassie blue and SDS. See Henderson, et al., *Anal. Biochem.* 93(1):153–7 (1979). Ion-pair extraction yielded good recoveries (96% recovery range=86–104%, n =3) of an enzymatically active 49 kDa protein. In a velocity reaction, ion-pair extracted 49 kDa form of exoenzyme S possessed a specific activity for the ADP-ribosylation of soybean trypsin inhibitor that approached the specific activity of native exoenzyme S (FIG. 2).

Figure 2:
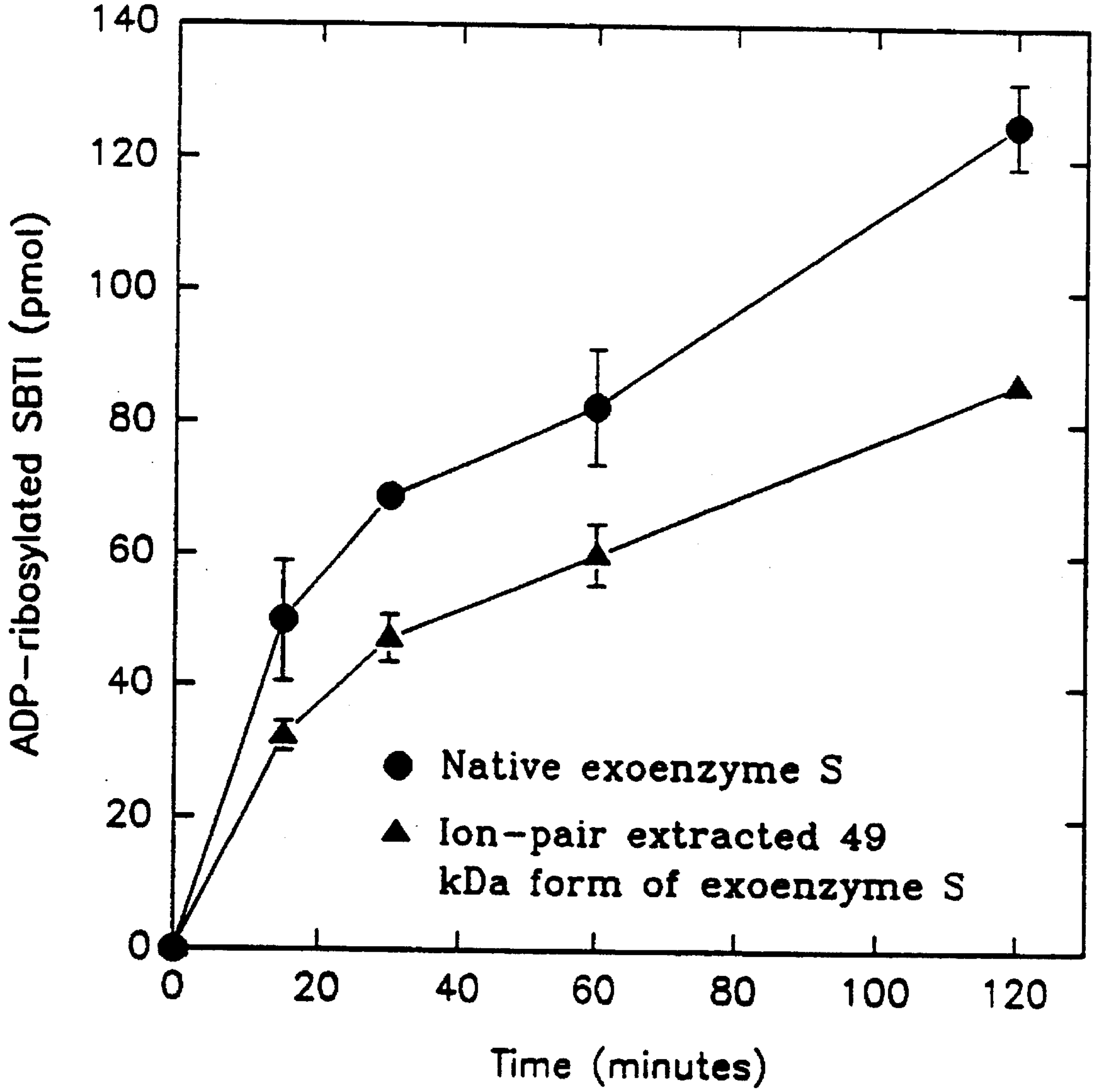
FIG. 2 depicts the ADP-ribosyltransferase activity of a native exoenzyme S and an ion-pair extracted 49 kDa form of exoenzyme S.

FIG. 2 is a graph of the ADP-ribosyltransferase activity of native exoenzyme S and ion-pair extracted 49 kDa form of exoenzyme S. Native exoenzyme S and ion-pair extracted 49 kDa form of exoenzyme S were normalized to the amount of 49 kDa protein present by AMBIS densitometry of Coomassie stained 10% SDS-PAGs. Native exoenzyme S (●) and ion-pair extracted 49 kDa form of exoenzyme S (Δ) containing equivalent amounts of 49 kDa protein (0.3 pmol) were assayed for their ability to ADP-ribosylate soybean trypsin inhibitor (SBTI). Data points are the mean of duplicate samples (error bars=standard error of the mean).

Proteolysis of Purified 49 kDa Form of Exoenzyme S.

Figure 3A:
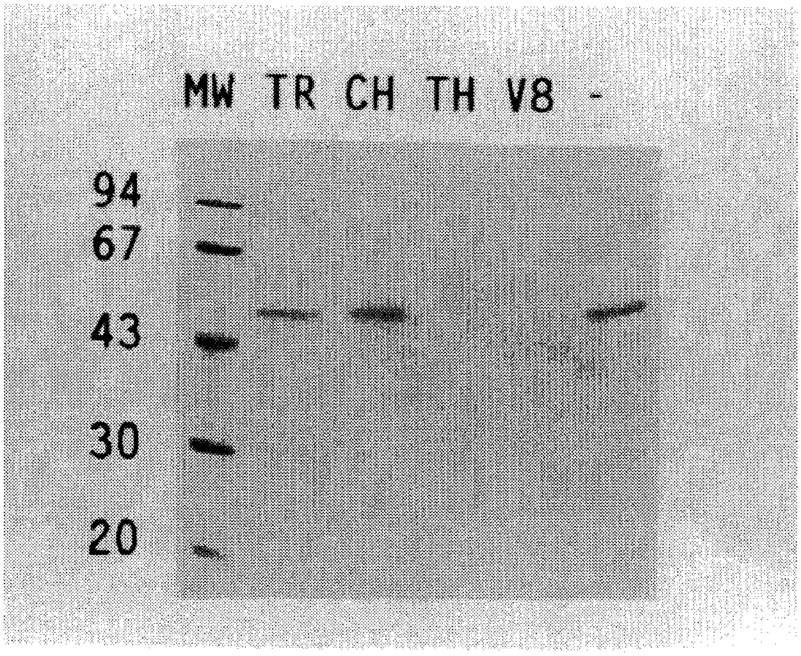
FIG. 3 depicts the proteolysis of a purified 49 kDa form of exoenzyme S.
Figure 3B:
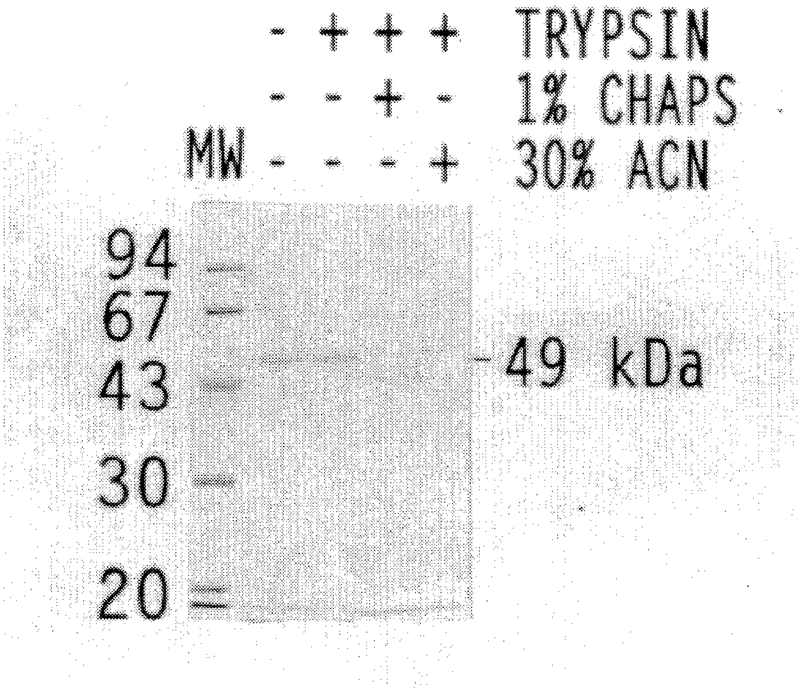

FIG. 3 demonstrates the proteolysis of purified 49 kDa form of exoenzyme S. FIG. 3 indicates the purified 49 kDa form of exoenzyme S (0.3 μg) was incubated for 24 h at 37° C. alone (–) or with 10% (w/w) trypsin (TR), chymotrypsin (CH), thermolysin (TH), or Staphylococcal V8 protease (V8). Samples were subjected to 10% reduced SDS-PAGE and gels were stained for total protein with Coomassie blue. Lane MW indicates molecular weight standards of 94, 67, 43, 30, and 20 kDa. FIG. 3*b* depicts the purified 49 kDa form of exoenzyme S (0.2 μg), digested with 10% (w/w) trypsin for 17 h at 37° C. Variables in the reaction included the presence (+) or absence (–) of trypsin, 1% CHAPS, and 30% acetonitrile (ACN). Samples were assessed for proteolysis of the 49 kDa form of exoenzyme S as described for panel a. At a 1:10 (w/w) ratio of protease to purified 49 kDa form of exoenzyme S, V8 protease and thermolysin degraded purified 49 kDa form of exoenzyme S. In contrast, neither trypsin nor chymotrypsin degraded purified 49 kDa form of exoenzyme S (FIG. 3*a*). Addition of 1% CHAPS or 30% ACN increased the susceptibility of purified 49 kDa form of exoenzyme S to proteolysis by trypsin (FIG. 3*b*) or chymotrypsin.

Limited proteolysis of diphtheria toxin and Pseudomonas exotoxin A, two bacterial ADP-ribosyltransferases, generates stable catalytic peptides. See Kandel, et al., *J. Biol. Chem.* 249(7):2088–97 (1974) and Lory, et al., *Infect. Immun.* 28(2):494–501 (1980). None of the aforementioned proteases degraded purified 49 kDa form of exoenzyme S to a stable proteolytic peptide. In addition, preincubation of purified 49 kDa form of exoenzyme S with NAD and/or FAS protein contained within a wheat germ extract did not stabilize a proteolytic peptide of purified 49 kDa form of exoenzyme S.

Tryptic Digestion of Ion-Pair Extracted 49 kDa Form of Exoenzyme S.

Conditions were defined to allow tryptic degradation of purified 49 kDa form of exoenzyme S (FIG. 3*b*). However, the presence of Coomassie blue in the preparation of purified 49 kDa form of exoenzyme S interfered with the analysis of tryptic peptides during RP-HPLC. An ion-pair extraction protocol was used to remove both Coomassie blue and SDS from purified 49 kDa form of exoenzyme S. See Henderson, et al., *Anal. Biochem.* 93(1):153–7 (1979). Trypsin digestion of ion-pair extracted 49 kDa form of exoenzyme S also required either 30% ACN or 1% CHAPS. Preparative tryptic digestion of ion-pair extracted 49 kDa form of exoenzyme S was performed in the presence of 30% ACN since, unlike CHAPS, ACN does not possess a significant absorbance at 215 nm which would interfere with detection of tryptic peptides.

Figure 4:
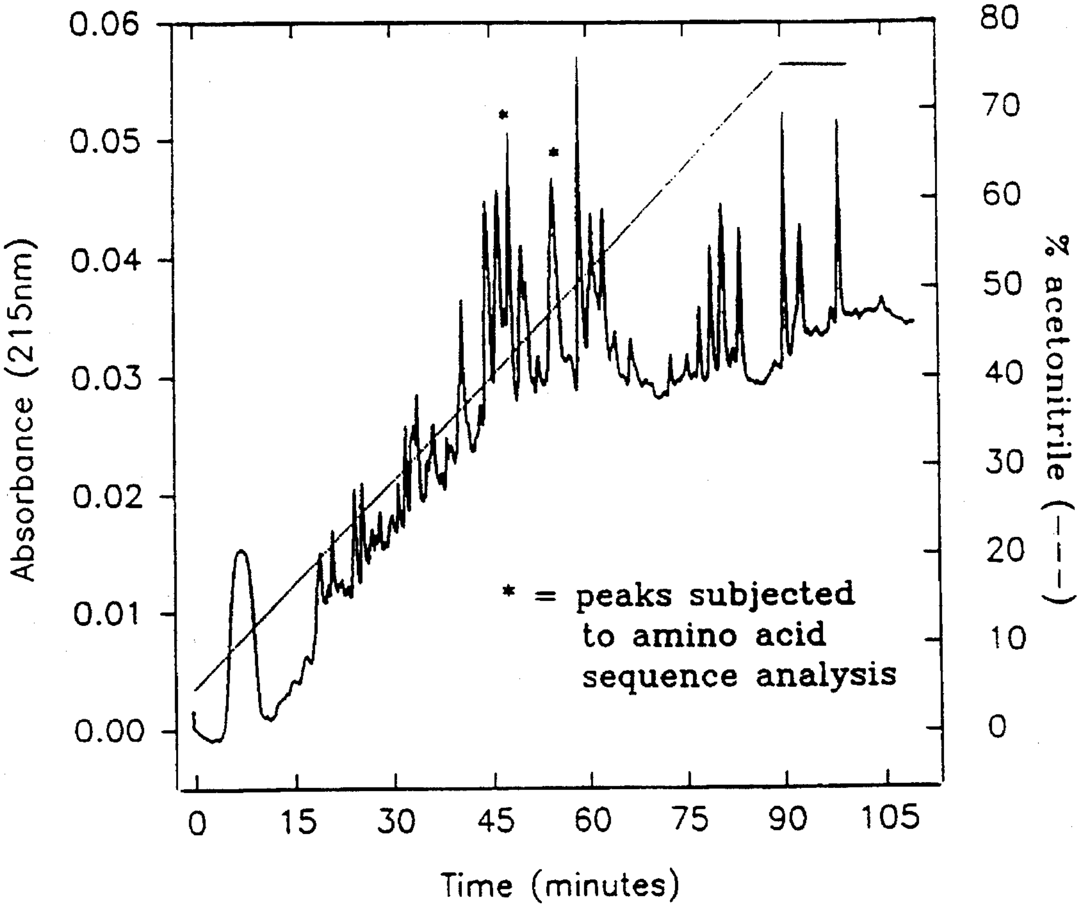
FIG. 4 depicts the Reverse phase-HPLC analysis of a tryptic digest of an ion-paired extracted 49 kDa form of exoenzyme S.

Consistent with its determined amino acid composition, Hunkapiller, et al., *Methods In Enzymology.* 91(227):227–36 (1983), trypsin digestion of ion-pair extracted 49 kDa form of exoenzyme S (126 pmol) yielded a complex profile of peptides (FIG. 4). FIG. 4 is a reverse phase-HPLC (RP-HPLC) analysis of a tryptic digest of ion-pair extracted 49 kDa form of exoenzyme S. Ion-pair extracted 49 kDa form of exoenzyme S (140 pmol) was incubated at 37° C. in the presence of 30% acetonitrile (ACN) with 10% (w/w) trypsin for 16 h, followed by an additional 10% trypsin for 4 h. The tryptic digest was diluted to. 7.5% ACN, acidified to 1% trifluroacetic acid (TFA), and 126 pmoles of the digest were subjected to RP-HPLC. Tryptic peptides, monitored by absorbance at 215 nm, were resolved using a Beckman μbondapak column (5 μm particle size) with a 5%–75% ACN gradient (dashed line) in 0.1% TFA at a flow rate of 1.0 ml/min. * indicates the 48 and 55 min tryptic peptides which were subjected to amino acid sequence analysis.

Of several tryptic peptides subjected to amino acid sequence analysis, the amino acid sequence of two tryptic peptides, which eluted at 48 min and 55 min, were obtained. Amino acid sequence analysis yielded a recovery of 58 pmol of Ser in the first cycle of sequencing of the 48 min peptide and 59 pmol of Val in the first cycle of sequencing the 55 min tryptic peptide, representing a 46% recovery of each peptide. The amino acid sequence of the 48 min tryptic peptide was S-F-G-Q-G-T-I-S-T-V-F-G-R (SEQ ID NO: 7), while the amino acid sequence of the tryptic peptide eluting at 55 min was V-L-E-E-A-A-L-G-E-Q-S-G-X-G-Q-G-L-L-D-A-L-D-X-A-S-K (SEQ ID NO 8). Since a basic amino acid was recovered as the final sequencing cycle, it was assumed that each peptide sequence represented a complete tryptic peptide. Searches of Genebank database (version 8) utilizing the FASTA algorithm showed that both tryptic peptides were unique. Another tryptic peptide was also detected during the sequencing of the 48 min tryptic peptide. The amino acid sequence of this peptide was G-L-D-K and the first residue of this peptide showed a yield of 30 pmol. Apparently, the elution of this peptide overlapped with the 48 min tryptic peptide.

Amplification of Two Nucleic Acid Probes Specific for the 49 kDa Form of Exoenzyme S.

DraI linearized DNA from *Pseudomonas aeruginosa* strain 388 was amplified with degenerate oligonucleotides that were designed to amplify DNA encoding the amino terminus or an internal region of the 49 kDa form of exoenzyme S.

Amplification of the 388 chromosomal template with degenerate oligonucleotides designed to amplify DNA encoding the amino terminus yielded a DNA fragment which possessed a 59-base pair (bp) open reading frame. Translation of this nucleotide sequence yielded the first 19 amino terminal amino acids of the 49 kDa form of exoenzyme S. See Kulich, et al., *Infect. Immun.* 61(1):307–13 (1993). This probe was termed the amino-terminal probe.

Amplification with degenerate oligonucleotides encoding the sense strand of the 55 min tryptic peptide and the antisense strand of the 48 min tryptic peptide did not yield a specific DNA fragment. In contrast, amplification with degenerate oligonucleotides encoding the sense strand of the 48 min tryptic peptide and the antisense strand of the 55 min tryptic peptide yielded a DNA fragment which encoded a 179-bp open reading frame. Translation of this nucleotide sequence yielded 12 amino acids of the 48 min tryptic peptide and 7 amino acids of the 55 min tryptic peptide. Consistent with the specificity of trypsin was the presence of an arginine residue immediately amino-terminal to the first amino acid of the 55 minute tryptic peptide. This probe was termed the internal probe.

Identification of P. Aeruginosac Chromosomal Dna Fragments Specific for the 49 kDa Form of Exoenzyme S.

Figure 5:
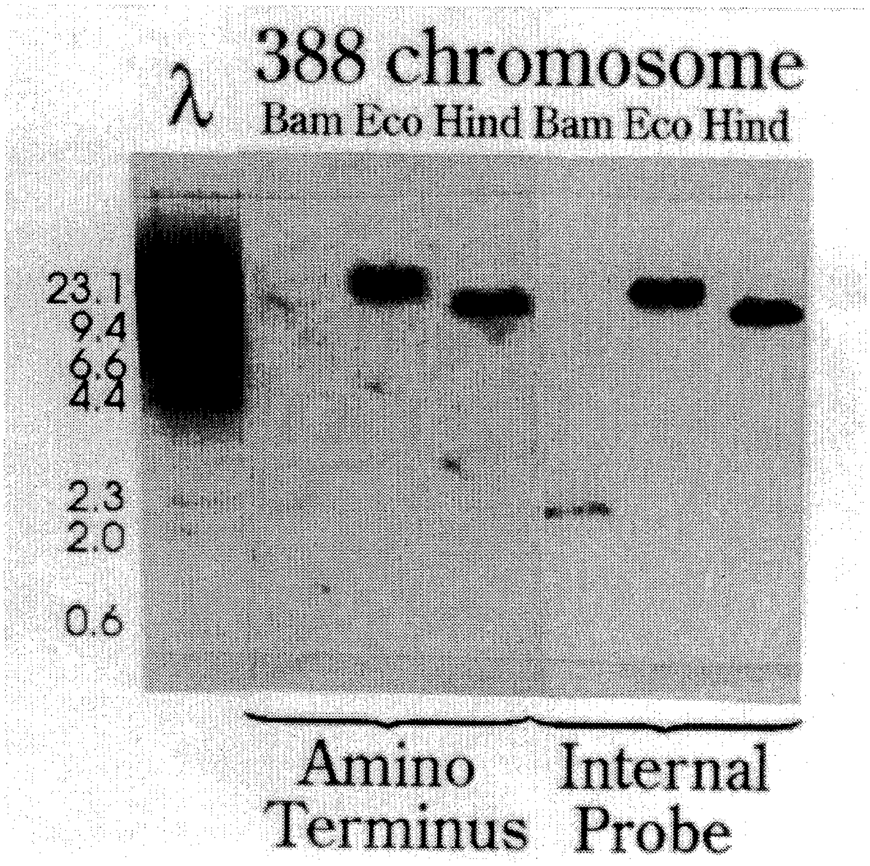
FIG. 5 represents a Southern blot of chromosomal DNA of *Pseudomonas aeruginosa* strain 388 with amino-terminal and internal probes of the 49 kDa form of exoenzyme S.

Both the amino-terminal probe and the internal probe hybridized to identical molecular weight DNA fragments of BamHI (2.3 kpb), EcoRI (>9.4 kbp), and HindIII (>9.4 kbp) digested Pseudomonas strain 388 chromosomal DNA (FIG. 5). FIG. 5 is a Southern blot of chromosomal DNA of *Pseudomonas aeruginosa* strain 388 with amino-terminal and internal probes of the 49 kDa form of exoenzyme S. *Pseudomonas aeruginosa* strain 388 chromosomal DNA was digested with BamHI (Bam), EcoRI (Eco), or HindIII (Hind) and subjected to Southern blotting using the amino-terminal probe or the internal probe. Lane γ represents a Southern blot of HindIII digested γ that was hybridized to itself. To the left of the γ lane are the molecular weights of the DNA fragments of HindIII digested γ in kbp. An autoradiogram of the Southern blot is shown. Exposure times were adjusted to allow detection of each hybridization.

Under the stringency conditions used, the amino-terminal probe and internal probe hybridized to one DNA fragment which indicated that there was one copy of the gene encoding the 49 kDa form of exoenzyme S.

Cloning the Gene Encoding the 49 kDa Form of Exoenzyme S (exoS) From A Cosmid Library of P. Aeruginop strain 388 Chromosomal DNA.

A pLAFR cosmid library composed of 2000 transformants was screened for homologous sequences by hybridization to the internal probe of the 49 kDa form of exoenzyme S. Eleven internal probe-positive transformants were identified and subjected to further analysis. Southern blotting of the isolated cosmid DNA showed that 8 of the 11 transformants possessed identical hybridization profiles to both the amino-terminal probe and internal probe. Southern blot analysis of BantHI, EcoRI, or HindIII digested cosmid DNA from these 8 transformants with the amino-terminal and internal probes yielded an identical hybridization profile as observed in the Southern Blot analysis of *Pseudomonas aeruginosa* strain 388 chromosomal DNA digested with the respective restriction enzymes (FIG. 5).

Restriction Map and Nucleotide Sequence of the DNA Encoding the 49 kDa Form of Exoenzyme S (exoS).

Figure 6A:
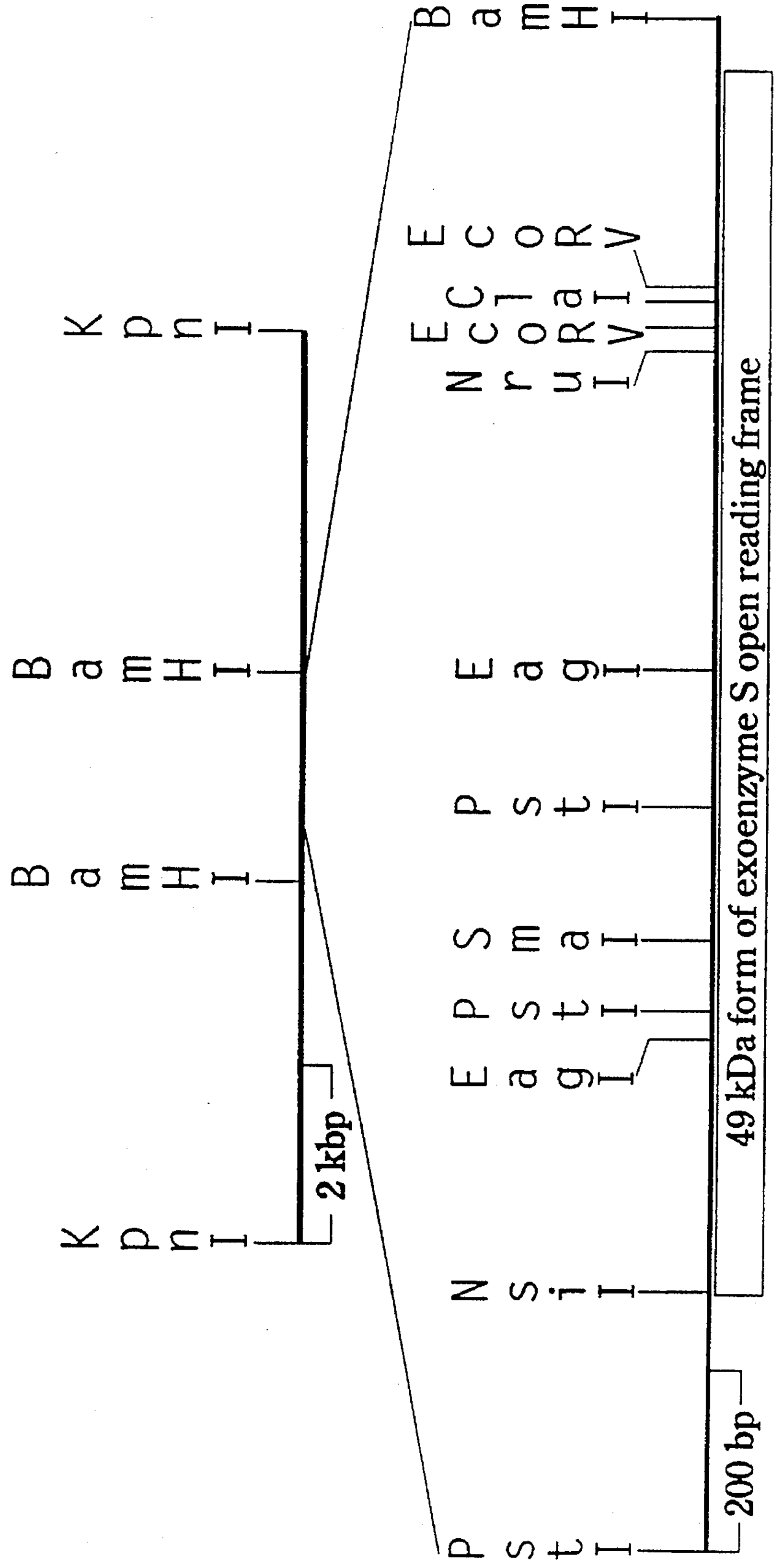

SEQ ID No: 1 reports the nucleic acid sequence of the exoS clone. FIG. 6 is a restriction endonuclease map and nucleotide sequence of exoS. FIG. 6*a* is a map of the KpnI chromosomal DNA fragment and the internal 2.3 kpb BamHI DNA fragment from *Pseudomonas aeruginosa* strain 388 is illustrated. The amino-terminal probe and internal probe hybridized to both DNA fragments. A restriction map of 1712 bp of the 2.3 kpb BamHI fragment is shown; not included is a 600 bp BamHI-PstI fragment which lies 5' to the 1712 bp pictured. FIG. 6B and 6C is the nucleotide sequence of the 1712 bp DNA fragment. The predicted amino acid sequence of EXOS is listed below the corresponding nucleotide sequence. The amino acid sequence of the amino terminus and the 48 min, 55 min, and G-L-D-K tryptic peptides that were determined by protein sequencing are underlined in the predicted amino acid sequence of EXOS. The locations and orientations of the primers used in the DNA amplification of the amino-terminal probe and the internal probe are shown as arrowed lines above the corresponding nucleotide sequence within exoS. A region of the nucleotide sequence that is consistent with the consensus *Pseudomonas aeruginosa* ribosome binding site, Shine, et al., Nature 254:34–8 (1975), lies within the double underlined region.

Homology searches with the FASTA algorithm did not align (within the top 40 alignments) EXOS to other bacterial ADP-ribosyltransferases. Using the seven primary amino acid sequences that have been shown to comprise the active site of *E. coli* heat-labile enterotoxin (LT), Sixma, et al., *Nature* 351:371–7 (1991), and other ADP-ribosyltransferases the BESTFIT algorithm, identified three regions of primary amino acid homology between EXOS and LT. This algorithm also showed that one of these alignments was common between EXOS and several members of the family of bacterial ADP-ribosyltransferases (FIG. 7).

Figure 7:
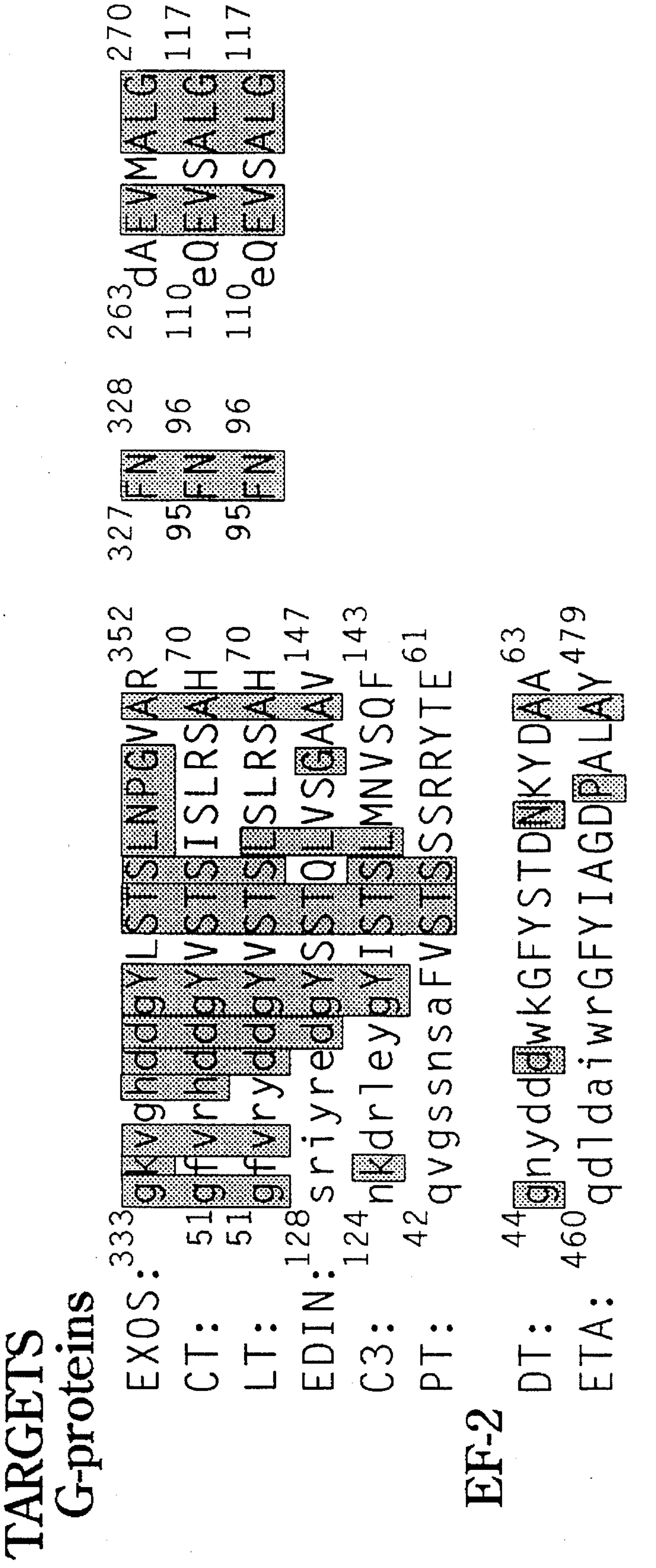
FIG. 7 represents the BESTFIT alignment of the 49 kDa form of exoenzyme S and members of the bacterial ADP-ribosyltransferase family. These sequences are identified in the Sequence Listing below as SEQ ID NO: 9–

FIG. 7 is a BESTFIT alignment of 49 kDa form of exoenzyme S and members of the bacterial ADP-ribosyltransferase family. Active site regions that were predicted from the crystal structures (denoted by upper case letters) of *E. coli* heat-labile enterotoxin (LT), Sixma, et al., *Nature* 351:371–7 (1991), *Pseudomonas aeruginosa* exotoxin A (ETA), Allured, et al., *Proc. Natl. Acad. Sci. U.S.A.* 83:1320–4 (1986), and diphtheria toxin (DT), Choe, et al., *Nature* 357:216–22 (1992), were used to identify regions of amino acid sequence homology in the 49 kDa form of exoenzyme S (EXOS), cholera toxin A chain (CT), Mekalanos, et al., *Nature* 306:551–7 (1983), *Clostridium botulinum exoenzyme* C3 (C3), Popoff, et al., *Nuc. Acids Res.* 18:1291 (1990), *S. aureus* epidermal cell differentiation inhibitor (EDIN), Inoue, et al., *Biochem. Biophys. Res. Comm.* 174:45964 (1991), and the S1 subunit of pertussis toxin (PT), Nicosia, et al., *Proc. Natl. Acad. Sci. U.S.A.* 83:4631–35 (1986), using the BESTFIT alignment program. Amino acid sequence homology extending beyond the active sites are indicated in lower case letters. Hatched boxes indicate regions of amino acid identity between EXOS and the indicated ADP-ribosyltransferase.

Creation of A Genetic Construct Capable of Expressing Exoemzyme S Activity

To create a genetic construct capable of expressing exoenzyme S activity, one would typically combine a coding region for exoenzyme S activity with appropriate regulatory sequences. Typically, appropriate regulatory sequences would include a promoter sequence (to promote translation of a protein product from a coding sequence) and a termination signal (to ensure termination at an appropriate point on the coding sequence). Vectors with appropriate expression signals for use in mammalian and bacterial cells are well known to those of skill in the art. For example, pT7-7 and pSVL would be suitable expression vectors. Alternatively, one may wish to express the construct of the present invention in either yeast or plant cells. Appropriate expression vectors for use in these organisms are well known to those of skill in the art.

The coding sequence disclosed at SEQ ID NO: 1 is one example of a sequence sufficient to encode exoenzyme S activity. However, this sequence may be modified somewhat and still retain exonenzyme S activity. For example, point mutations and small deletions and insertions may still leave the sequence capable of expressing exoenzyme S activity. One would typically evaluate a candidate nucleic acid sequence in terms of its ability to express a protein product capable of exoenzyme S activity and the physical characteristics of the expressed protein product.

If one wishes to evaluate a candidate sequence for exoenzyme S activity, one would perform the assay described above after expressing a candidate genetic construct in an expression system. An exoenzyme S activity level of 160 mol/min/mol 49 kDa or above would indicate an appropriate genetic coding sequence.

DISCUSSION

This study described the purification and proteolytic characterization of the 49 kDa form of exoenzyme S and the cloning of its structural gene (exoS) from *Pseudomonas aeruginosa* strain 388. The 49 kDa form of exoenzyme S was purified from native exoenzyme S using SDS-PAGE followed by electroelution. Earlier prior art preparations of the 49 kDa form of exoenzyme S contained small amounts (about 10%) of the 53 kDa form of exoenzyme S. See Coburn, et al., *J. Biol. Chem.* 266(10):6438–46 (1991). In contrast, preparations of the 49 kDa form of exoenzyme S used in the present study did not contain detectable amounts of the 53 kDa form of exoenzyme S as measured by either Coomassie blue staining, silver staining, or immunoblot analysis using antisera that recognized both the 53 and 49 kDa forms of exoenzyme S.

Analysis of purified 49 kDa form of exoenzyme S for exoenzyme S activity showed that it lacked any detectable exoenzyme S activity. This was inconsistent with studies by Iglewski and Nicas, Nicas, et al., *Infect. Immun.* 45(2):470–4 (1984), and Gill and coworkers, Coburn, et al., *J. Biol. Chem.* 266(10):6438–46 (1991), which demonstrated that the 49 kDa form of exoenzyme S possessed exoenzyme S activity following elution from SDS-PAGs. We believe that our preparations of purified 49 kDa form of exoenzyme S lacked exoenzyme S activity due to the presence of SDS in our samples following electroelution, since SDS inhibits exoenzyme S activity. Following extraction of SDS from our preparations of purified 49 kDa form of exoenzyme S, ion-pair extracted 49 kDa form of exoenzyme S expressed exoenzyme S activity with a specific activity that was about 70% of native exoenzyme S. These data showed that with respect to the native form of exoenzyme S, the 49 kDa form of exoenzyme S was sufficient for expression of the ADP-ribosyltransferase activity associated with exoenzyme S.

Purified 49 kDa form of exoenzyme S was less susceptible to the serine proteases trypsin and chymotrypsin than to Staphyloccocal V8 protease and thermolysin. The resistance to trypsin or chymotrypsin was not expected since we had observed that the 49 kDa protein present in native exoenzyme S preparation was readily degraded by trypsin and chymotrypsin. The protease resistance of purified 49 kDa form of exoenzyme S did not appear to be due to inhibition by SDS because addition of either 30% ACN or 1.0% CHAPS increased its susceptibility to trypsin and chymotrypsin. Also, ion-pair extraction of purified 49 kDa form of exoenzyme S, which removed SDS, did not increase the protein's susceptibility to trypsin.

Trypsin-digested ion-pair extracted 49 kDa form of exoenzyme S produced a complex mixture of tryptic peptides. Database comparison of the 48 and 55 minute tryptic peptides showed that the two peptide sequences were unique which, coupled with the high recovery of these peptides during amino acid sequencing (about 46%), argued that these peptides were components of the 49 kDa form of exoenzyme S and not the product of a minor contaminating protein present in the ion-pair extracted 49 kDa form of exoenzyme S.

A 2.3 kpb BamHI DNA fragment isolated from a *Pseudomonas aeruginosa* strain 388 cosmid library contained exoS. Nucleotide sequence analysis showed that exoS was composed of a 1362 bp open reading frame which encoded a protein of 453 amino acid with a predicted molecular mass of 48,302 daltons. This molecular mass was consistent with the reported molecular mass of the 49 kDa form of exoenzyme S. The predicted isoelectric point of EXOS was 5.8 which agreed with the acidic nature of the 49 kDa form of exoenzyme S as determined by isoelectric focusing of native exoenzyme S. With the exception of proline residues, the predicted amino acid composition of EXOS paralleled that of the 49 kDa form of exoenzyme S. See Kulich, S. M., Frank, D. W., and Barbieri, J. T. (1993) *Infect. Immun.* 61(1):307–13. In addition, the predicted amino acid sequence of EXOS contained the amino-terminal amino acid sequence and the three tryptic peptide sequences that were determined to be components of the 49 kDa form of exoenzyme S. Consistent with the specificity of trypsin, each tryptic peptide was preceded by a basic amino acid in the predicted amino acid sequence of EXOS. These data are consistent with this open reading frame being the structural gene for the 49 kDa form of exoenzyme S. We are currently pursuing the expression of exoS in both *E. coli* and Pseudomonas.

Exoenzyme S has been proposed to exist in two forms, an enzymatically inactive 53 kDa form and an enzymatically active 49 kDa form. See Nicas, et al., *Infect. Immun.* 45(2):470–4 (1984). Several observations are consistent with these proteins being related including: immunological cross-reactivity, Nicas, et al., (supra) and Kulich, et al., (supra); common proteolytic peptides, Iglewski, (supra); common proteolytic peptides, See Iglewski, (supra) similar amino acid compositions, and a common amino-terminal amino acid sequence, see Coburn, (supra). It has been proposed that the 53 kDa form is proteolyzed at the carboxyl-terminus yielding the enzymatically active 49 kDa form. See. Coburn, (supra). If the 49 kDa form of exoenzyme S arises from proteolysis of the 53 kDa form of exoenzyme S, our studies define the maximum site of this carboxyl-terminal degradation to be no greater than at amino acid residue 431 of exoenzyme S. This is defined by the fact that the 55 min trypsin peptide of ion-pair extracted 49 kDa form of exoenzyme S lies 23 amino acid residues from the carboxyl-terminus of EXOS. Current studies are directed at defining the molecular and biochemical relationship between the 53 and 49 kDa forms of exoenzyme S.

Homology studies showed that EXOS was unique. This analysis also showed that EXOS did not contain a reported cyanogen bromide peptide that was used to clone exoenzyme S from *Pseudomonas aeruginosa* strain DG1. See Sokol, et al., *Microb. Pathog.* 8(4):243–57 (1990). This showed that exoS, which we have cloned from *Pseudomonas aeruginosa* strain 388, was different from that cloned from *Pseudomonas aeruginosa* strain DG1. See Sokol, et al., *Microb. Pathog.* 8(4):243–57 (1990). The FASTA algorithm did not assign a high degree of homology between the 49 kDa form of exoenzyme S and the other bacterial ADP-ribosyltransferases.

Hol and coworkers (Sixma, et al., *Nature* 351:371–7 (1991)) showed that although there was little conservation within the primary amino acid sequences of the active sites of LT and exotoxin A, the three dimensional structure of the two active sites were superimpossible. Using the BESTFIT algorithm, we attempted to align the seven regions of LT and exotoxin A which comprise the three dimensional structure of their active sites with EXOS. As shown in FIG. 7, sequences within EXOS aligned with three of the seven regions of the active site of LT. From this alignment, it appears that there is a high degree of homology between residues 333 and 352 of EXOS and several members of the family of bacterial ADP-ribosyltransferases which modify heterotrimeric- and low-molecular-weight-GTP binding proteins.

This BESTFIT algorithm also aligned E265 of EXOS with E112 of LT. Cieplak and coworkers showed that mutations at E112 reduced the catalytic activity of LT. See Lobet, et al., *Infect. Immun.* 59:2870–9 (1991). E112 appears to be homologous to E148 of diphtheria toxin which has been implicated as an active site residue. Together, these data make E265 of EXOS a candidate active site glutamic acid in the ADP-ribosyltransferase reaction.

One nuance to this BESTFIT alignment is that the three regions of primary amino acid homology are in the opposite orientation for EXOS relative to LT and cholera toxin. This may indicate that exoS has evolved from a different evolutionary pathway towards the generation of a common active site with respect to these other bacterial ADP-ribosyltransferases.

A weight matrix analysis of the amino terminus of EXOS suggests that a signal peptidase cleavage site exists between two alanine residues at positions 19 and 20. See yon Heijne, *Nucleic Acids Res.* 14(11):4683–4690 (1986). However, the amino acid residues preceding the cleavage site do not form a hydrophobic core that is characteristic of signal sequences, yon Heijne (1985) *J. Mol Biol.* 184:99–105. Amino-terminal sequence analysis of purified 49 kDa form of exoenzyme S and the deduced amino-terminal sequence from exoS are identical, which indicates that an amino-terminal sequence is not cleaved from the 49 kDa form of exoenzyme S during secretion into the culture medium. We have also observed that exoenzyme S synthesis and secretion is normal in a strain of *Pseudomonas aeruginosa* that lacks signal peptidase activity and fails to secrete exotoxin A, elastase, phospholipase C, and pilin, Strom, et al., *J. Bacteriol.* 173(3):1175–1180 (1991). Together, these data indicate that exoenzyme S secretion from Pseudomonas is independent of the general secretion pathway.

ADDITIONAL EMBODIMENTS OF THE PRESENT INVENTION

Development of a Vaccine From Modified a ExoS Gene

Site specific mutations will be introduced in the exoS gene to produce a non-catalytic but immunogenic molecule. The catalytic activity of this molecule would be reduced by a factor of $10^4$–$10^6$-fold. Comparison of the amino acid sequences between exoS and other ADP-ribosyltransferases indicate that common catalytic residues could be targeted for site-specific mutations that reduce ADP-ribosyltransferase activity. The chances of reversion will be minimized by the introduction of several mutations within the exoS coding region. Recombinant, enzymatically inactive forms of exoenzyme S will be expressed in *Escherichia coli*. Subcellular fractionation and purification of the recombinant forms of exoenzyme S will be used to produce an acellular vaccine candidate.

Vaccine strains of *Pseudomonas aeruginosa* that express enzymatically inactive forms of exoS will be constructed utilizing allelic replacement procedures (Frank, et al., *Infec. Immun.* 62:in press (1994)). Recombinant genes will be returned to the chromosomes of *Pseudomonas aeruginosa* strains that lack exotoxin A activity for production of a cellular vaccine. Potential recipients of either vaccine include persons at high risk for burn wounds (military and fire prevention personnel), cystic fibrosis patients, leukemic, and neutropenic individuals.

Development of a Chemotherapeutic Agent

Activation of ras in eukaryotic cells appears to be a factor in uncontrolled growth of cancerous cells. Obtaining the cloned exoS gene allows the construction of immunotoxin molecules for specific targeting to tumor cells or the direct treatment of cancerous cells with DNA encoding exoenzyme S. Entry of the protein or DNA followed by ADP-ribosylation of ras by exoenzyme S may result in the disruption of the pathway to uncontrolled growth.

Development of a Diagnostic Tool

Intensive care patients who receive mechanical ventilation and burn patients whose bacterial burden exceeds 105 per gram of skin tissue are at high risk for developing fatal septicemic *Pseudomonas aeruginosa* infections. Expression of exoenzyme S correlates with the spread of *Pseudomonas aeruginosa* from epithelial colonization sites to the bloodstream of infected individuals. Detection of the exoS gene or messenger RNA by nucleic acid hybridization techniques with patient material may lead to earlier therapeutic intervention to reduce the loss of life due to gram-negative septicemia.

Development of Passive Protective Reagents

Human monoclonal antibodies will be developed that specifically neutralize exoenzyme S activity. Cystic fibrosis patients with high titered antibodies to exoenzyme S will be the source of blood cells for fusions to human myeloma cells. Antibody-producing cell lines will be screened for reactivity to purified, recombinant exoenzyme S by enzyme-linked immunoassay. Purified antibodies will be tested for the ability to neutralize exoenzyme S activity in vitro. Further studies will utilize acute animal infection models to screen for antisera that neutralize exoenzyme S toxicity. These reagents will be used to treat *Pseudomonas aeruginosa* infected patients to neutralize exoenzyme S and prevent fatal septicemia associated with the spread of bacteria to the bloodstream.

Although the present invention has been described with reference to certain preferred embodiments, other versions are possible. Thus, the invention is not to be limited to just the specific embodiments described. The claims should be examined to judge the full scope of the invention.

We claim:

1. A method of detecting the presence of *Pseudomonas aeruginosa* infection, comprising the steps of (a) obtaining a nucleic acid sample from a patient;

(b) exposing said sample to a probe under conditions whereby said probe hybridizes with any target sequence present in said sample, said probe comprised of a DNA sequence encoding exoenzyme S according to SEQ ID NO: 1; and (c) detecting hybridization as an indication of *Pseudomonas aeruginosa* infection.

2. A vector containing a coding region for the 49 kDa form of exoenzyme S from *Pseudomonas aeruginosa* , wherein the sequence of the coding region is SEQ ID NO: 1.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 1712 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
CTGCAGGCTG AGTACGCTCT CCTCGTCATT GGGCGTCGGG AGATCGAGAG CGAGAAAAAG    60
CTGGTGGATG GCGGCGCGGT AGAGTGGATT CATGGCGTGT TCCGAGTCAC TGGAGGCGGC   120
CATTAGAGCA GTGCCAGCCC GGAGAGACTG TTAATCGTGG TTCTCTTTTT TTAGGTTTTG   180
CCGCTGCCGA TTCCAGTGAA AAAACGGCGG CCAATCCTGA TAGGCGATGG GGTTTCCCGT   240
TCCTAGACTG GCGGAGAAAC ATCAGGAGAA GGCAACCATC ATGCATATTC AATCGCTTCA   300
GCAGAGTCCG TCTTTCGCCG TCGAATTGCA CCAGGCCGCC AGTGGGCGTT TGGGACAGAT   360
TGAGGCCCGC CAGGTCGCCA CCCCCAGTGA AGCGCAGCAG TTGGCCCAGC GCCAGGACGC   420
GCCGAAGGGT GAGGGGCTGC TCGCTCGCCT GGGCGCGGCG CTCGTGCGTC CGTTCGTGGC   480
GATCATGGAC TGGCTGGGCA AACTGTTGGG CTCCCACGCC CGCACCGGCC CGCAGCCCAG   540
TCAGGACGCG CAGCCTGCGG TCATGTCCTC GGCCGTCGTG TTCAAGCAGA TGGTGCTGCA   600
GCAGGCATTG CCCATGACCT TGAAGGGACT CGACAAGGCG AGCGAGCTGG CGACCCTGAC   660
ACCGGAAGGA CTGGCCCGGG AGCACTCCCG CCTGGCCAGC GGAGATGGGG CGCTGCGTTC   720
GCTGAGCACC GCCTTGGCCG GCATTCGTGC CGGCAGCCAG GTCGAGGAGT CCCGTATCCA   780
GGCTGGCCGC CTGCTCGAAC GGAGCATCGG CGGGATCGCG CTGCAGCAGT GGGGCACCAC   840
CGGCGGTGCC GCGAGTCAAC TGGTGCTCGA CGCAAGCCCG GAACTGCGGC GCGAAATCAC   900
CGACCAGTTG CATCAGGTAA TGAGCGAGGT CGCACTGTTG CGCCAAGCGG TAGAGAGCGA   960
GGTCAGCAGA GTATCGGCCG ACAAGGCGCT GGCGGATGGC CTGGTGAAGC GGTTCGGGGC  1020
GGATGCGGAA AAGTACCTGG GCAGACAGCC TGGTGGCATC CACAGTGACG CCGAAGTGAT  1080
GGCGCTTGGT CTCTACACCG GCATTCACTA CGCGGACCTG AATCGCGCTC TGCGTCAGGG  1140
GCAGGAGCTG GATGCGGGAC AAAAGCTGAT CGACCAAGGT ATGTCCGCGG CCTTCGAGAA  1200
GAGCGGACAG GCTGAACAGG TAGTGAAGAC TTTCCGTGGC ACCCGTGGCG GGGATGCCTT  1260
CAACGCAGTG GAAGAGGGCA AGGTTGGCCA CGACGACGGC TATCTCTCCA CCTCCCTGAA  1320
CCCCGGTGTC GCGAGGAGCT TCGGGCAGGG CACGATATCC ACCGTGTTCG GCAGGTCCGG  1380
AATCGATGTC AGCGGGATAT CGAACTACAA GAATGAAAAA GAGATTCTCT ATAACAAAGA  1440
AACCGACATG CGCGTGCTGC TGAGCGCCAG CGATGAGCAG GGAGTGACCC GCCGGGTTCT  1500
CGAAGAGGCG GCCCTGGGGG AGCAGAGTGG CCATAGCCAG GGACTGCTCG ATGCTCTCGA  1560
CCTGGCAAGC AAACCGGAAC GTTCAGGCGA GGTCCAGGAA CAGGATGTAC GCCTGAGGAT  1620
GCGCGGCCTT GATCTGGCCT GACCGGTCGT AAAAGAAAGA CGTCACGAAC GGACACCTTG  1680
GGGTGTCCGA TTCTTGGCTC GGCAGCGGAT CC                                1712
```

( 2 ) INFORMATION FOR SEQ ID NO:2:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO:2:

CATGGATCCG AATTCATGCA YATCCARATC CARTCSYT 38

( 2 ) INFORMATION FOR SEQ ID NO:3:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO:3:

CATGGATTCG AATTCGARCT SCAYCARGCS GC 32

( 2 ) INFORMATION FOR SEQ ID NO:4:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO:4:

TTCGGYCARG GYACSAT 17

( 2 ) INFORMATION FOR SEQ ID NO:5:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO:5:

TGYTCRCCSA GSGCSGC 17

( 2 ) INFORMATION FOR SEQ ID NO:6:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO:6:

CCSAGSGCSG CYTCYTC 17

( 2 ) INFORMATION FOR SEQ ID NO:7:

( i ) SEQUENCE CHARACTERISTICS:
( A ) LENGTH: 13 amino acids
( B ) TYPE: amino acid
( C ) STRANDEDNESS: single -continued ( D ) TOPOLOGY: lincar ( i i ) MOLECULE TYPE: protein ( x i ) SEQUENCE DESCRIPTION: SEQ ID NO:7:

Ser Phe Gly Gln Gly Thr Ile Ser Thr Val Phe Gly Arg
1 5 10

( 2 ) INFORMATION FOR SEQ ID NO:8:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Val Leu Glu Glu Ala Ala Leu Gly Glu Gln Ser Gly Xaa Gly Gln Gly
1 5 10 15

Leu Leu Asp Ala Leu Asp Xaa Ala Ser Lys
20 25

( 2 ) INFORMATION FOR SEQ ID NO:9:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Gly Lys Val Gly His Asp Asp Gly Tyr Leu Ser Thr Ser Leu Asn Pro
1 5 10 15

Gly Val Ala Arg
20

( 2 ) INFORMATION FOR SEQ ID NO:10:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Gly Phe Val Arg His Asp Asp Gly Tyr Val Ser Thr Ser Ile Ser Leu
1 5 10 15

Arg Ser Ala His
20

( 2 ) INFORMATION FOR SEQ ID NO:11:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Gly Phe Val Arg Tyr Asp Asp Gly Tyr Val Ser Thr Ser Leu Ser Leu 1 5 10 15

Arg Ser Ala His
20

( 2 ) INFORMATION FOR SEQ ID NO:12:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Ser Arg Ile Tyr Arg Glu Asp Gly Tyr Ser Ser Thr Gln Leu Val Ser
1 5 10 15

Gly Ala Ala Val
20

( 2 ) INFORMATION FOR SEQ ID NO:13:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Asn Lys Asp Arg Leu Glu Tyr Gly Tyr Ile Ser Thr Ser Leu Met Asn
1 5 10 15

Val Ser Gln Phe
20

( 2 ) INFORMATION FOR SEQ ID NO:14:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Gln Val Gly Ser Ser Asn Ser Ala Phe Val Ser Thr Ser Ser Ser Arg
1 5 10 15

Arg Tyr Thr Glu
20

( 2 ) INFORMATION FOR SEQ ID NO:15:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Gly Asn Tyr Asp Asp Asp Trp Lys Gly Phe Tyr Ser Thr Asp Asn Lys
1 5 10 15

Tyr Asp Ala Ala
20

(2) INFORMATION FOR SEQ ID NO:16:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:16:

```
Gln Asp Leu Asp Ala Ile Trp Arg Gly Phe Tyr Ile Ala Gly Asp Pro
1               5                   10                  15

Ala Leu Ala Tyr
            20
```

(2) INFORMATION FOR SEQ ID NO:17:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

```
Asp Ala Glu Val Met Ala Leu Gly
1               5
```

(2) INFORMATION FOR SEQ ID NO:18:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

```
Glu Gln Glu Val Ser Ala Leu Gly
1               5
```

(2) INFORMATION FOR SEQ ID NO:19:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

```
Glu Gln Glu Val Ser Ala Leu Gly
1               5
```